(12) United States Patent
Melman (10) Patent No.: US 9,441,010 B2
(45) Date of Patent: Sep. 13, 2016

(54) METHOD FOR SELECTIVE DERIVATIZATION OF OLIGOHISTIDINE SEQUENCE OF RECOMBINANT PROTEINS

(71) Applicant: Artem Melman, Potsdam, NY (US)

(72) Inventor: Artem Melman, Potsdam, NY (US)

(73) Assignee: CLARKSON UNIVERSITY, Potsdam, NY (US)

( * ) Notice: Subject to any disclaimer, the term of this patent is extended or adjusted under 35 U.S.C. 154(b) by 121 days.

(21) Appl. No.: 13/962,426

(22) Filed: Aug. 8, 2013

(65) Prior Publication Data

US 2014/0046040 A1    Feb. 13, 2014

Related U.S. Application Data

(60) Provisional application No. 61/680,821, filed on Aug. 8, 2012.

(51) Int. Cl.
*C07K 1/13* (2006.01)
*C07C 69/736* (2006.01)
*C07K 1/107* (2006.01)

(52) U.S. Cl.
CPC .............. *C07K 1/13* (2013.01); *C07C 69/736* (2013.01); *C07K 1/107* (2013.01)

(58) Field of Classification Search
None
See application file for complete search history.

(56) References Cited

FOREIGN PATENT DOCUMENTS

| EP | 2031394 | * | 4/2009 | ............... C07K 1/22 |
| GB | WO/2009/047500 | * | 4/2009 | ............. A61K 47/48 |

OTHER PUBLICATIONS

Abts et al., Rational and Irrational Approaches to Convince a Protein to Crystallize, (published online Jan. 2012) Dr. Nikolai Kolesnikov (Ed.), InTech, Available from: http://www.intechopen.com/ books/modern-aspects-of-bulk-crystal-and-thin-film-preparation/rational-andirrational-approaches-to-convince-a-protein-to-crystallize.*

* cited by examiner

*Primary Examiner* — Marcela M Cordero Garcia
*Assistant Examiner* — Catherine Mader
(74) *Attorney, Agent, or Firm* — Bond, Schoeneck & King, PLLC; Blaine Bettinger; George McGuire (57) ABSTRACT

Methods and compositions for the selective derivatization of a oligohistidine-tagged recombinant protein. A modifying compound comprised of an imidazole reactive group, a linker, and a ligating group is contacted with the recombinant protein, and a cooperative bond forms between the ligating group and the oligohistidine tag in the presence of a metal cation, and a covalent bond forms between the imidazole reactive group and an imidazole ring of the oligohistidine tag followed by the concomitant separation of the imidazole reactive group from the linker. Addition of a metal chelator results in the dissociation of the ligating group and the oligohistidine tag.

11 Claims, 6 Drawing Sheets

METHOD FOR SELECTIVE DERIVATIZATION OF OLIGOHISTIDINE SEQUENCE OF RECOMBINANT PROTEINS

CROSS-REFERENCE TO RELATED APPLICATIONS

This application claims priority to U.S. Provisional Patent Application Ser. No. 61/680,821, filed on Aug. 8, 2012 and entitled "Method for Selective Derivatization of Oligohistidine Sequence of Recombinant Proteins," the entire disclosure of which is incorporated herein by reference.

BACKGROUND

The present invention relates to methods for modification of proteins and, more specifically, to methods for the chemical derivatization of proteins.

The most common method of preparation of proteins involves preparation of recombinant DNA plasmid encoding the desired amino acid sequence, introduction of the recombinant DNA into prokaryotic or eukaryotic cells, and expression of the encoded protein in the cells. To simplify subsequent purification of these proteins recombinant DNA sequences commonly incorporate a nucleotide sequence encoding an oligohistidine tag at the beginning or at the end of the polypeptide chain. During purification of recombinant proteins the oligohistidine sequence is bound on chromatography columns functionalized by aminocarboxylate groups binding divalent metal cations resulting in its separation from other proteins that does not contain oligohistidine sequences.

Chemical derivatization of native and recombinant proteins is used for modification of their physical, chemical, and biological properties, and for their immobilization on interfaces. Existing methods of chemical derivatization of proteins involve formation of covalent bonds with amino acid residues of the polypeptide chain of proteins using reactions of alkylation, acylation, formation of thioureas, formation of mixed disulfides, as well as other reactions. These reactions are frequently not selective and provide complex mixtures of products.

BRIEF SUMMARY

Systems and methods for selective chemical reaction with an oligohistidine tag in a recombinant protein resulting in selective chemical modification of proteins. According to one aspect is a method for the selective derivatization of a recombinant protein comprising the steps of: (i) contacting a recombinant protein comprising a oligohistidine tag with a modifying compound in the presence of a metal cation, wherein the modifying compound comprises, for example, the formula $X_1X_2X_3$ wherein $X_1$ is an imidazole reactive group, $X_2$ is a linking group, and $X_3$ is at least one ligating group; wherein the imidazole reactive group comprises a functional group, an electron withdrawing group, and a connector connecting the imidazole reactive group to $X_2$; and further wherein the contacting is performed under conditions sufficient for the formation of a coordinative bond between $X_3$ and the oligohistidine tag utilizing the metal cation, and under conditions sufficient for the formation of a covalent bond between $X_1$ and an imidazole ring of the oligohistidine tag and concomitant separation of $X_1$ and $X_2$; and (ii) breaking the bond between $X_3$ and the oligohistidine tag using a metal chelator.

According to an aspect, there is provided a imidazole reactive group represented by Formula (I) or (II) below:

where R is the functional group, R1 is the electron withdrawing group, and R2 is the linking group. According to one embodiment, $X_3$ comprises a plurality of ligating groups.

According to another aspect, the electron withdrawing group is selected from the group consisting of an acyl group, an ester group, a carbamyl group, an alkylsulfonyl group, an arylsulfonyl group, a nitro group, a cyano group, and combinations thereof.

According to yet another aspect, the functional group is selected from the group consisting of a fluorophore, an azido group, an alkyne group, an alkene group, a diene group, a triene group, a biotin residue, a phenyl, a substituted phenyl, a polycyclic aromatic group, an aromatic heterocyclic group, a polycyclic aromatic heterocyclic group, a radioactive group, a group that possess distinct magnetic properties, and combinations thereof.

According to one embodiment, $X_3$ is selected from the group consisting of a primary amino group, a secondary amino group, a teriary amino group, a carboxy group, an imino group, a phenol group, a catechol group, a hydroxamate group, a sulfamido group, a phosphoryl group, an imidazolyl group, a thiazolyl group, an oxazolyl group, a pyridazolyl group, a pyridyl group, a thiol group, and combinations thereof.

According to another aspect, the metal cation is selected from the group consisting of $Ni^{2+}$, $Zn^{2+}$, $Cu^{2+}$, $Fe^{2+}$, $Co^{2+}$, $Co^{3+}$, $Fe^{3+}$, and combinations thereof. According to one embodiment, the conditions sufficient for the formation of a coordinative bond between $X_3$ and the oligohistidine tag comprise the presence of an additive, which can be, for example, imidazole, N-methylimidazole, or N-alkylimidazole.

According to an aspect is a compound for the selective derivatization of a recombinant protein comprising a oligohistidine tag, the compound comprising the formula $X_1X_2X_3$ wherein $X_1$ is an imidazole reactive group, $X_2$ is a linking group, and $X_3$ is at least one ligating group, further wherein the imidazole reactive group comprises a functional group, an electron withdrawing group, and a connector connecting the imidazole reactive group to $X_2$, and further wherein the compound is adapted to form a bond between $X_3$ and a oligohistidine tag of a recombinant protein in the presence of a metal cation, and further adapted to form a covalent bond between $X_1$ and an imidazole ring of the oligohistidine tag.

According to one aspect the imidazole reactive group of the compound or the selective derivatization of a recombinant protein comprising a oligohistidine tag comprises the structure represented by Formula (I) below:

where R is the functional group, R1 is the electron withdrawing group, and R2 is the linking group.

According to an aspect, the functional group is selected from the group consisting of an azido group, an alkyne group, an alkene group, a diene group, a triene group, a biotin residue, a phenyl, a substituted phenyl, a polycyclic aromatic group, an aromatic heterocyclic group, a polycyclic aromatic heterocyclic group, and combinations thereof.

According to one embodiment, $X_3$ is selected from the group consisting of a primary amino group, a secondary amino group, a teriary amino group, a carboxy group, an imino group, a phenol group, a catechol group, a hydroxamate group, a sulfamido group, a phosphoryl group, an imidazolyl group, a thiazolyl group, an oxazolyl group, a pyridazolyl group, a pyridyl group, a thiol group, and combinations thereof.

According to an aspect is a method for selective derivatization of a recombinant protein, the method comprising the steps of: (i) contacting a recombinant protein comprising a oligohistidine tag with a modifying compound in the presence of a divalent metal cation, wherein the modifying compound comprises the formula $X_1X_2X_3$, wherein $X_1$ is an imidazole reactive group comprising the structure represented by Formula (I) or (II) below:

wherein R is a functional group, R1 is an electron withdrawing group selected from the group consisting of an acyl group, an ester group, an alkylsulfonyl group, an arylsulfonyl group, a nitro group, a cyano group, and combinations thereof, and R2 is a linking group; $X_2$ is the linking group; and $X_3$ is a plurality of ligating groups each selected from the group consisting of a primary amino group, a secondary amino group, a teriary amino group, a carboxy group, a phosphoryl group, an imidazolyl group, a thiazolyl group, an oxazolyl group, a pyridazolyl group, a pyridyl group, and combinations thereof; and further wherein the contacting is performed under conditions sufficient for the formation of a bond between $X_3$ and the oligohistidine tag utilizing a metal cation, and under conditions sufficient for the formation of a covalent bond between $X_1$ and an imidazole ring of the oligohistidine tag and concomitant separation of $X_1$ and $X_2$; and (ii) breaking the bond between $X_3$ and the oligohistidine tag using a metal chelator.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION

Figure 1:
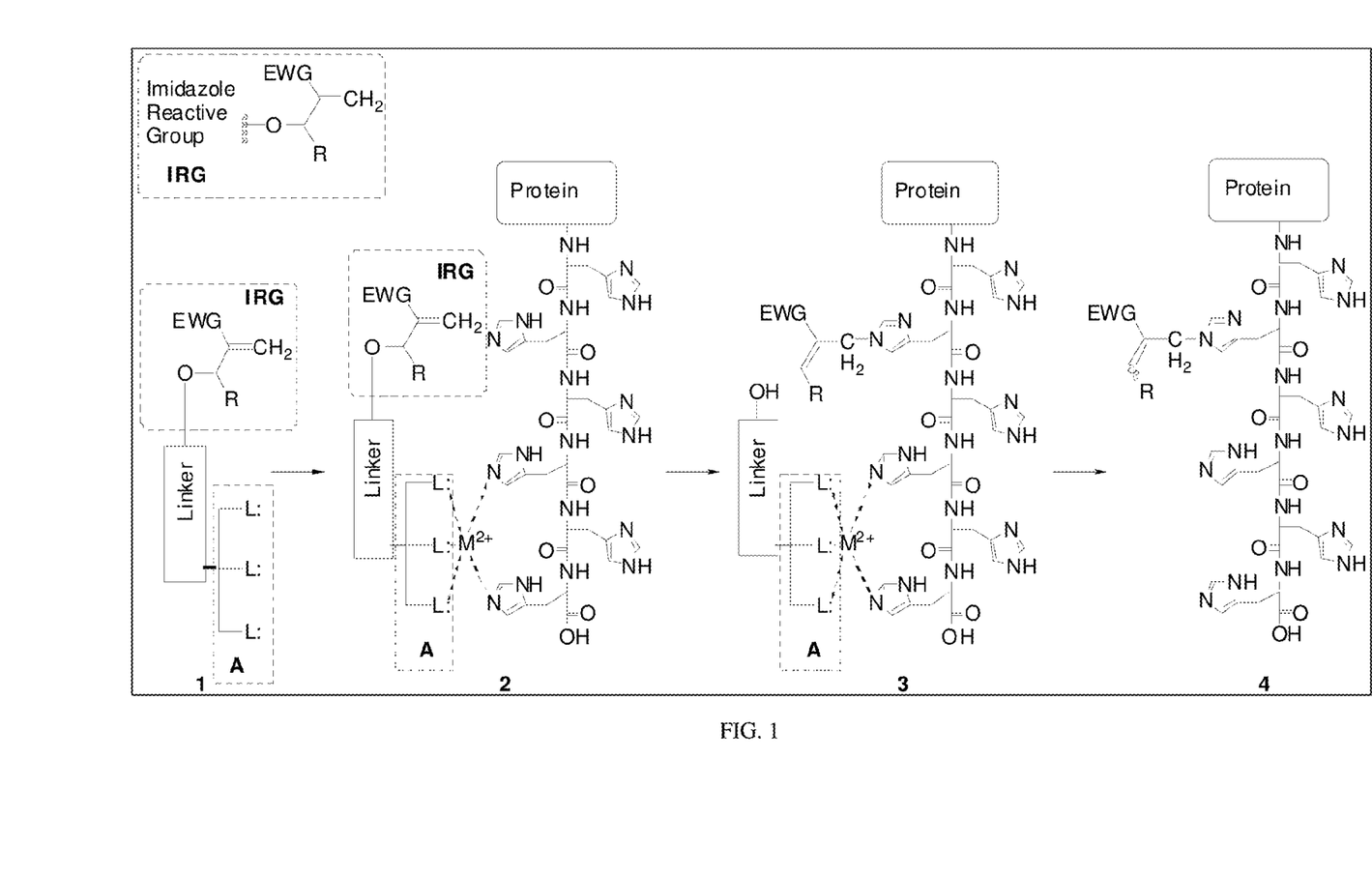
FIG. 1 is a schematic representation of a reaction scheme for the synthesis of a selective derivatization of an oligohistidine sequence of a recombinant protein according to an embodiment.

Referring now to the drawings, wherein like reference numerals refer to like parts throughout, there is seen in FIG. 1 a schematic representation of a reaction scheme for the synthesis of a selective derivatization of an oligohistidine sequence of a recombinant protein according to an embodiment. According to an aspect of the invention are methods and systems for selective chemical reaction with an oligohistidine tag in a recombinant protein resulting in selective chemical modification of that protein.

According to another aspect are novel chemical reagents possessing at least two different functional groups. The first functional group, depicted as group "A" in FIG. 1, comprises one, two, three, or more ligating components depicted as "L:". These ligating groups are adapted to be capable of coordinative binding through a divalent metal cation $M^{2+}$ to an oligohistidine tag present in a recombinant protein. The second functional group, depicted as group "IRG" in FIG. 1, comprises an Imidazole Reactive Group ("IRG") which is adapted to be capable of selective alkylation of an imidazole ring of a histidine residue of the oligohistidine tag through an addition-elimination process. According to an embodiment, these two functional groups (A and IRG) are connected by covalent bonds to a linker as represented by, for example, structure 1 in FIG. 1 and structure 5 in FIG. 2. Because the coordinative binding is specific to an oligohistidine tag that is rarely present in polypeptide chains of proteins, the disclosed method allows selective derivatization of the oligohistidine sequence in the presence of other amino acid residues in the same recombinant protein, and in the presence of other proteins, either naturally- or artificially-occurring.

In a first embodiment schematically represented in FIG. 1, functional groups A and IRG in structure 1 are connected through a carbon-oxygen bond that undergoes elimination on a subsequent step of the abovementioned process. The initial rapid and reversible coordinative binding of ligating groups L: in new reagents through the metal cation $M^{2+}$ to the oligohistidine tag produces mixed metal complex 2 shown in FIG. 1. The mixed metal complex 2 serves as a template for the subsequent addition-elimination reaction that results in the formation of a covalent bond between the IRG and one of the imidazole rings found in the histidine tag of the oligohistidine sequence, with concomitant break of the bond between the imidazole-reactive group and linker function to yield covalently modified protein of type 3 in FIG. 1. The coordination bonds between metal cation $M^{2+}$ and oligohistidine tag can be removed by addition of a strong metal chelator such as EDTA to yield a covalently modified protein of type 4 in FIG. 1.

According to an embodiment, the fragment IRG that remains covalently bound to the histidine tag can be covalently attached to other functionalities that can be used for subsequent specific covalent or non-covalent binding with other molecules and or other polymers.

According to an embodiment, the electron withdrawing group (abbreviated "EWG" in the figures and also known as a deactivating group) depicted in FIG. 1 and elsewhere herein may be, for example, any electron withdrawing group, including but not limited to acyl, ester, alkylsulfonyl, arylsulfonyl, aminosulfonyl, carbamoyl, alkoxycarbonyl, nitro, and/or cyano groups, among others. The "R" group depicted in FIG. 1 and elsewhere herein may be, for example, a phenyl, a substituted alkyl, a polycyclic aromatic group, an aromatic heterocyclic group, and/or a polycyclic aromatic heterocyclic group, aryl, heteroaryl, alkyl, acyl, ester, carbamino, sulfonyl, or alkylthio, among many other types of functional groups. R can carry other functional groups including but not limited to an azido group, alkyne group, diene group, triene group, or biotin residue, among others. The functional group may also be a group sufficient or capable of immobilizing the modified recombinant protein to a surface. For example, the immobilizing functional group can be an aromatic possessing group capable of specific binding to a surface.

According to an embodiment, the metal cations can be, for example, divalent or trivalent cations such as $Ni^{2+}$, $Zn^{2+}$, $Cu^{2+}$, $Fe^{2+}$, $Co^{2+}$, $Co^{3+}$, and/or $Fe^{3+}$, among many others. The "L:" can be, for example, a ligating component capable of forming coordinative bond with abovementioned metal cations including but not limited to primary, secondary, and teriary amino groups, carboxy, phosphoryl, imidazolyl, thiazolyl, oxazolyl, pyridazolyl, pyridyl, amido, sulfamido, triazolyl, and/or hydroxy groups, among many others. The linker can be, for example, a carbon chain, or a cyclic system, or a combination thereof capable of carrying one, two, three, four, or more ligating groups L: and covalently attached to the oxygen atom of the imidazole reacting group as disclosed herein, although other structures are possible.

According to another embodiment, the reaction comprises one or more additional optimal conditions suitable or necessary to improve and/or maximize the chemical yield of the reaction. These conditions include, for example, use of water as the main component of solvent, and/or the use of one or more chemical compounds capable of forming a coordinative bond with abovementioned metal cations. These additives can include, for example, imidazole, N-methylimidazole, and/or N-alkylimidazole, among many others.

Figure 2:
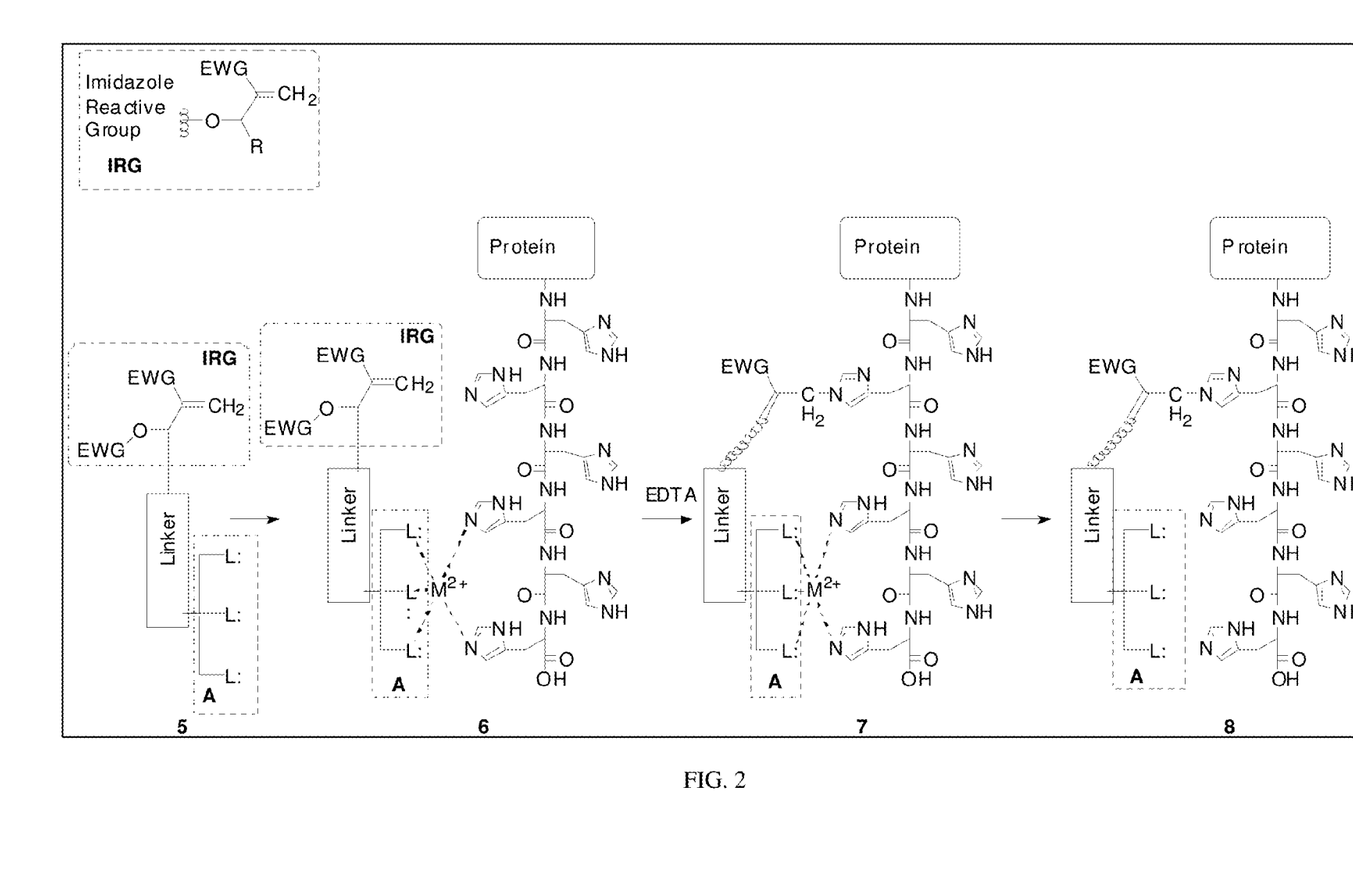
FIG. 2 is a schematic representation of a reaction scheme for the selective derivatization of an oligohistidine sequence of a recombinant protein according to an embodiment.

There is seen in FIG. 2 a schematic representation of a reaction scheme for the synthesis of a selective derivatization of an oligohistidine sequence of a recombinant protein according to another embodiment. In this embodiment, functional groups "A" and IRG are connected through a permanent covalent bond to produce reagents of type 5 in FIG. 2. According to this embodiment, this covalent bond is not cleaved in a subsequent stage. The initial rapid and reversible coordinative binding of ligating groups L: through the metal cation $M^{2+}$ to the oligohistidine tag of a recombinant produces mixed metal complex 6 in FIG. 2. The mixed metal complex 6 serves as a template for the subsequent chemical reaction of addition-elimination that forms a covalent bond between the IRG and one of imidazole rings of the oligohistidine tag with concomitant elimination of leaving group EWG-O, which permanently binds the group to the oligohistidine tag to yield covalently modified protein of type 7 in FIG. 2. Finally, the coordination bonds between metal cation $M^{2+}$ and oligohistidine tag in the resultant complex can be removed by treatment with a strong metal chelator such as EDTA to yield the covalently modified protein of type 8 in FIG. 2.

Figure 3:
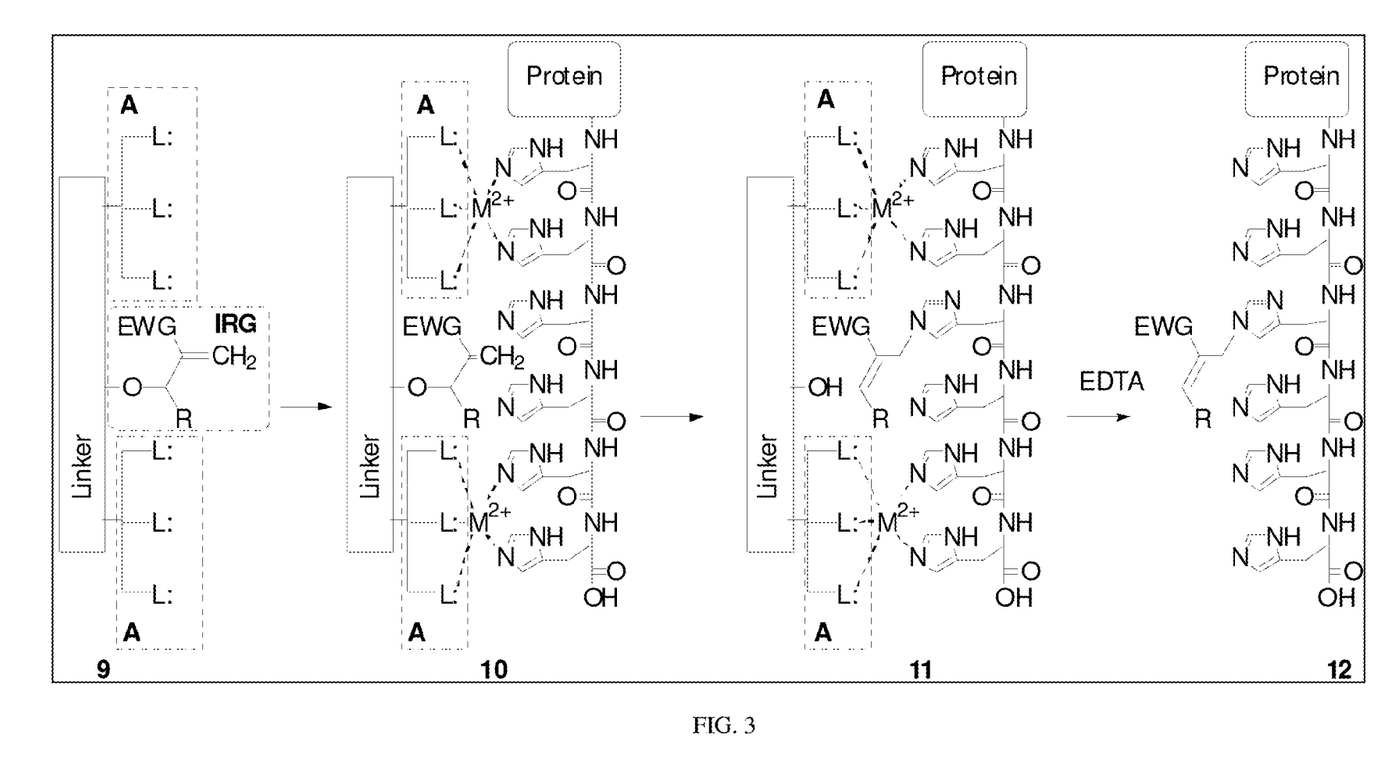
FIG. 3 is a schematic representation of a reaction scheme for the selective derivatization of an oligohistidine sequence of a recombinant protein according to an embodiment.

There is seen in FIG. 3 a schematic representation of a reaction scheme for the synthesis of a selective derivatization of an oligohistidine sequence of a recombinant protein according to another embodiment. In this embodiment, functional groups "A" and IRG are connected as shown in structure 9 of FIG. 3, through a carbon-oxygen bond that undergoes elimination on a subsequent step of the abovementioned process. The initial rapid and reversible coordinative binding of ligating groups L: through two metal cations $M^{2+}$ to the oligohistidine tag of a recombinant protein produces mixed metal complex 10 in FIG. 3. The mixed metal complex 10 serves as a template for the subsequent chemical reaction of addition-elimination that forms a covalent bond between the IRG and one of imidazole rings of the oligohistidine sequence with concomitant break of the bond between the imidazole-reactive group and linker function to yield covalently modified protein of type 11 in FIG. 3. Finally, the coordination bonds between metal cation $M^{2+}$ and oligohistidine tag can be removed through can be removed by a strong metal chelator such as EDTA to yield covalently modified protein of type 12 in FIG. 3.

Figure 4:
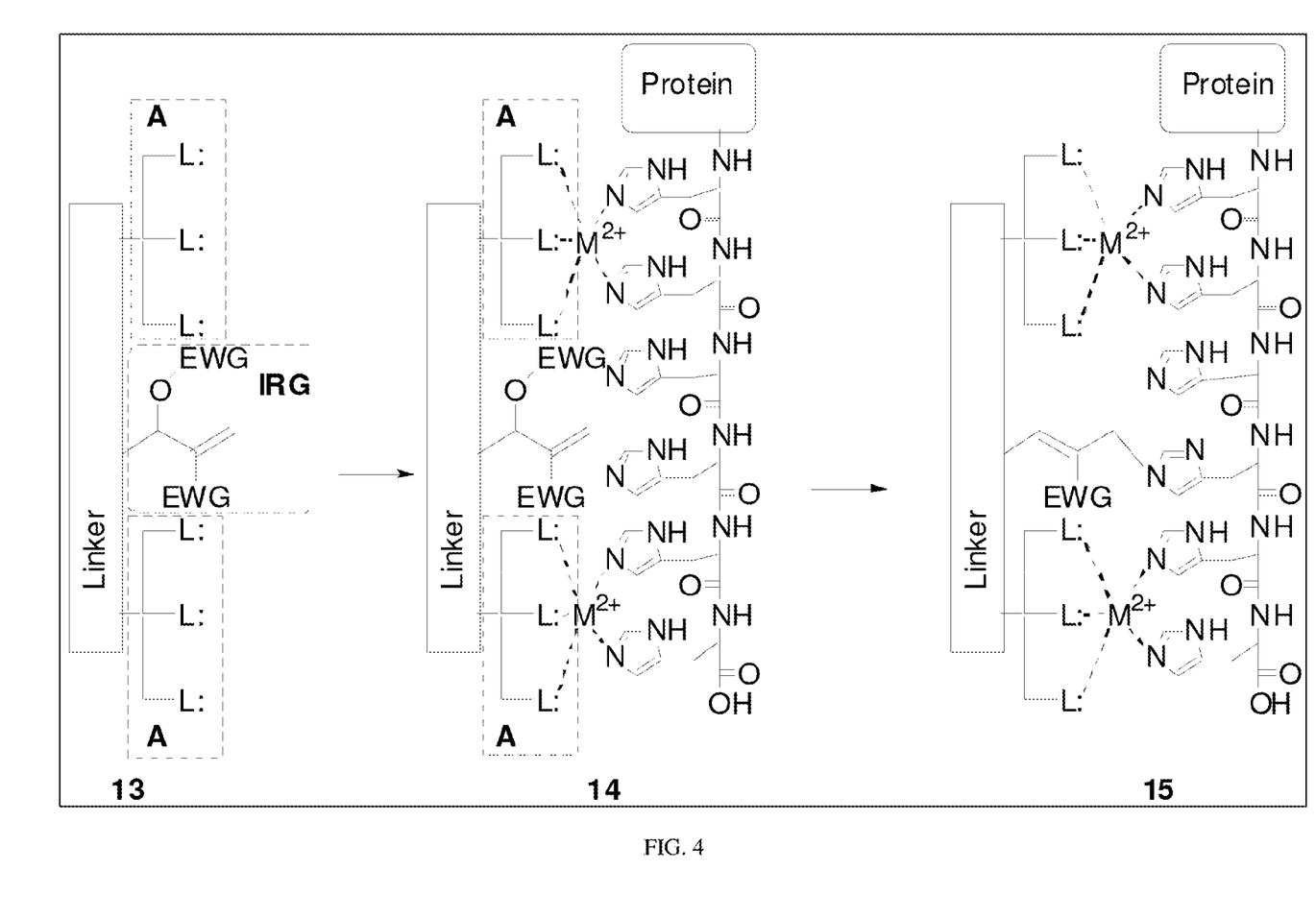
FIG. 4 is a schematic representation of a reaction scheme for the selective derivatization of an oligohistidine sequence of a recombinant protein according to an embodiment.

There is seen in FIG. 4 a schematic representation of a reaction scheme for the synthesis of a selective derivatization of an oligohistidine sequence of a recombinant protein according to another embodiment. In this embodiment, functional groups "A" and IRG are connected as shown in structure 9 of FIG. 3, through a carbon-oxygen bond that does not undergo elimination on a subsequent step of the abovementioned process. The initial rapid and reversible coordinative binding of ligating groups L: through two metal cations $M^{2+}$ to the oligohistidine tag of a recombinant protein produces mixed metal complex 14 in FIG. 4. The mixed metal complex 14 serves as a template for the subsequent chemical reaction of addition-elimination that form a covalent bond between the imidazole-reactive functional group IRG and one of imidazole rings of the oligohistidine sequence with concomitant break of the bond between the imidazole-reactive group and linker function to yield covalently modified protein of type 11 in FIG. 4. Finally, the coordination bonds between metal cation $M^{2+}$ and oligohistidine tag can be removed through can be removed by a strong metal chelator such as EDTA to yield covalently modified protein of type 12 in FIG. 3.

EXAMPLE 1

Figure 5:
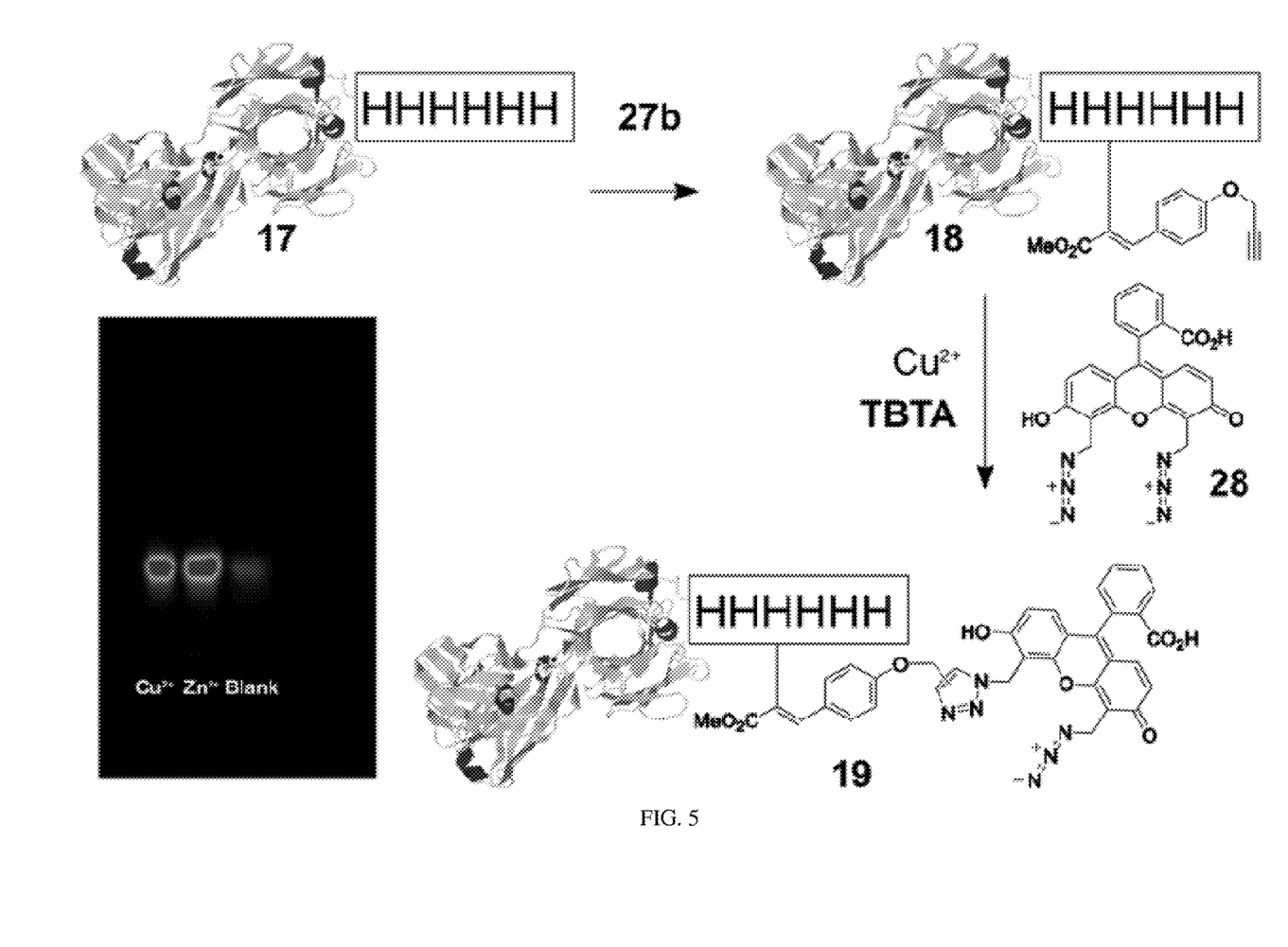
FIG. 5 is a schematic representation of a reaction scheme for the derivatization of a recombinant protein with a fluorescent group according to an embodiment.
Figure 6:
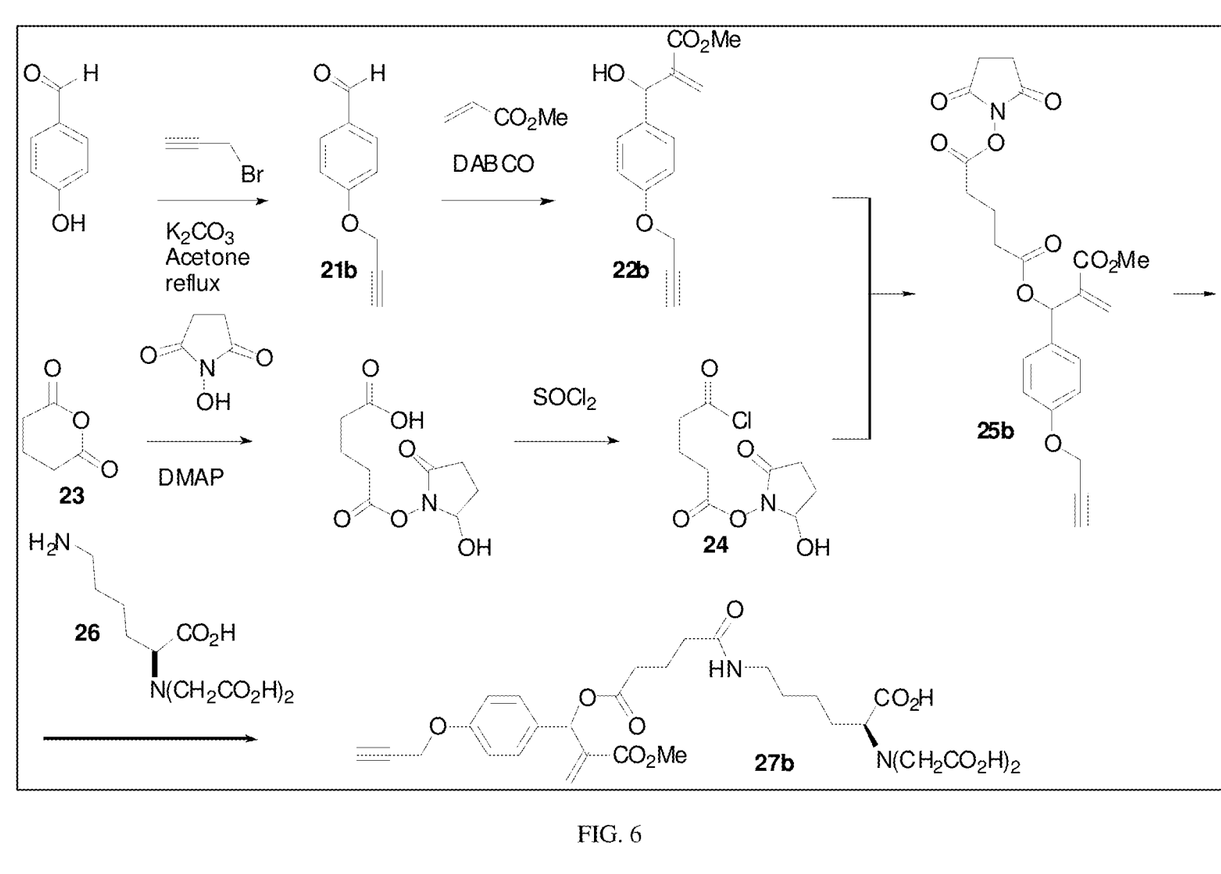
FIG. 6 is a schematic representation of a reaction scheme according to one embodiment for the synthesis of an ester used in the derivatization of a recombinant protein with a fluorescent group.

According to one embodiment is the covalent derivatization of a recombinant protein with a fluorescent group, a schematic representation of which is depicted in FIGS. 5 and 6. According to this example, recombinant protein 17 in FIG. 5 comprises an oligohistidine tag ("HHHHH"), and is derivatized with an alkynyl function through templated alkylation with an ester 27b (see also FIG. 6 for an example of the production of ester 27b) followed by a "click" cycloaddition with fluorescein azide 28 to produce fluorescent protein 19. Also shown in FIG. 5 is a scan of a fluorescent image of SDS electrophoresis of obtained samples of fluorescent protein 19 obtained by treatment with ester 27b (in the presence of $Cu^{2+}$ or $Zn^{2+}$, or in the absence of metal cations) all after reaction with fluorescent azide 28.

According to this example, compound 21b (4-Prop-2-ynyloxy-benzaldehyde) in FIG. 6 is produced by the following procedure. A mixture of 4-hydroxybenzaldehyde (6.1 g, 50 mmol), $K_2CO_3$ (27.6 g, 200 mmol), and propargyl bromide (80 wt %, 29.8 g, 21.6 ml, 200 mmol) in acetone was heated at reflux for 6 hours. After filtration, the filtrate was concentrated in vacuum. The resulting residue was dissolved in 120 ml $CH_2Cl_2$, washed with water, dried over $Na_2SO_4$, and concentrated in vacuum to yield title compounds (6.6 g, 82%) as a yellowish amorphous solid. $^1$H NMR (400 MHz, $CDCl_3$): δ 2.20 (s, 1H), 4.69 (s, 2H), 7.10 (d, J=8.4 Hz, 2H), 7.87 (d, J=8.8 Hz, 2H), 9.91 (s, 1H).

According to this example, compound 22b (Methyl 2-[Hydroxy-(4-prop-2-ynyloxy-phenyl)-methyl]acrylate) in FIG. 6 is produced by the following procedure. To a solution of aldehyde (4.8 g, 30 mmol) and methyl acrylate (15 ml) in 15 ml methanol was added DABCO (3.36 g, 30 mmol) with stirring at room temperature. The mixture was left in darkness for 48 hours. It was then concentrated in vacuum, the residue was dissolved in 150 ml ethyl acetate, washed with water, 1M HCl, and brine, respectively. It was then dried over $Na_2SO_4$, and concentrated in vacuum. The resulting oil was purified by flash chromatography (3:1 hexane/EtOAc) to yield A-135 (2.5 g, 34%) as an oil. $^1$H NMR (400 MHz, $CDCl_3$): δ 2.52 (t, J=2.4 Hz, 1H), 2.92 (d, J=5.6 Hz, 1H), 3.72 (s, 3H), 4.68 (d, J=2.4 Hz, 2H), 5.53 (d, J=5.2 Hz, 1H), 5.85 (s, 1H), 6.33 (s, 1H), 6.95 (d, J=8.8 Hz, 2H), 7.31 (d, J=8.4 Hz, 2H).

According to this example, compound 25b (Mono(1-(4-prop-2-ynyloxy-phenyl)-2-methoxycarbonyl-2-propenyl) glutaric acid N-hydroxy succinimide ester) in FIG. 6 is produced by the following procedure. To a solution of N-Hydroxysuccinimide (922 mg, 8 mmol) and DMAP (1466 mg, 12 mmol) in 120 ml dry THF was added glutaric anhydride 3 (914 mg, 8 mmol) portionwise with stirring at 0° C. The mixture was allowed warm to room temperature, and stirred for 4 hours and concentrated in vacuo. The residue was dissolved in 120 ml ethyl acetate, washed with 2 M HCl, brine, dried over $Na_2SO_4$. After filtration, the filtrate was concentrated in vacuo to yield 1.8 g solid of glutaric acid N-hydroxysuccinimide monoester that was dissolved in 8 ml anhydrous $CH_2Cl_2$ and treated with oxalyl chloride (1016 mg, 0.68 ml, 8 mmol) with stirring at 0° C. The reaction mixture was allowed to warm to room temperature, to which anhydrous DMF (30 µl) was added 1 hour later followed by stirring overnight at room temperature. The reaction mixture was concentrated to dryness in vacuum, dissolved in 6 ml anhydrous $CH_2Cl_2$, and added at 0° C. to a solution of alcohol 22b (1478 mg, 6 mmol) and anhydrous pyridine (950 mg, 0.97 ml, 12 mmol) in 10 ml anhydrous $CH_2Cl_2$. The mixture was allowed to warm to room temperature, stirred for 4 hours, diluted with 120 mL 1:3hexane/EtOAc (120 mL), washed with water, 1M HCl, saturated $NaHCO_3$, brine, and over $Na_2SO_4$. The residue was evaporated and the residue was separated by flash chromatography (1:1 hexane/EtOAc) to yield title compound (1.3 g, 47%) as an pale yellow oil. 1H NMR (400 MHz, $CDCl_3$): δ 2.04-2.11 (m, 2H), 2.51-2.55 (m, 3H), 2.68 (t, J=6.8 Hz, 2H), 2.85 (s, 4H), 2.73 (s, 3H), 4.69 (d, J=2 Hz, 2H), 5.88 (s, 1H), 6.40 (s, 1H), 6.68 (S, 1H), 6.96 (d, J=8.4 Hz, 2H), 7.33 (d, J=8.4 Hz, 2H). 13C NMR (100 MHz, $CDCl_3$): δ 19.79, 25.57, 29.88, 32.71, 52.04, 55.79, 72.75, 75.70, 78.42, 114.80, 125.64, 129.13, 130.64, 139.60, 157.63, 165.41, 168.01, 169.09, 171.16.

According to this example, compound 27b (Mono(1-(4-prop-2-ynyloxy-phenyl)-2-methoxycarbonyl-2-propenyl) glutaric acid 5S-carboxy-5-[bis(hydroxycarbonylmethyl) amino]pentylamide) in FIG. 6 is produced by the following procedure. To a mixture of NTA amine (131 mg, 0.5 mmol), and methanol (1 ml) was added triethylamine (101.2 mg, 0.14 ml, 1 mmol) to obtain a homogeneous solution, to which a solution of A-138B (5 ml, 0.1 M) in THF was added dropwise with stirring at 0° C. The mixture was allowed to warm to room temperature, and stirred overnight. It was then concentrated to dryness in vacuum. The residue was purified by flash chromatography (4:1 to 1:5 $CHCl_3/CH_3OH$) to yield B-071 (110 mg, 36%) as a solid. $^1$H NMR (400 MHz, $D_2O$): δ 1.21-1.70 (m, 6H), 1.86 (t, J=7.2 Hz, 3H), 2.18 (d, J=8.0 Hz, 2H), 2.44 (t, J=7.2 Hz, 2H), 2.92 (s, 1H), 3.00-3.20 (m, 6H), 3.70 (s, 3H), 4.78 (s, 2H), 5.98 (s, 1H), 6.45 (s, 1H), 6.55 (s, 1H), 7.04 (d, J=8.4 Hz, 2H), 7.39 (d, J=8.4 Hz, 2H). 13C NMR (100 MHz, $D_2O$): δ 8.21, 20.56, 23.74, 26.59, 28.12, 33.04, 34.65, 38.89, 46.63, 52.45, 55.86, 68.85, 73.40, 76.78, 78.56, 115.07, 127.41, 129.15, 130.39, 138.32, 157.09, 167.13, 170.52, 174.04, 175.23.

According to this example, compound 28 (4',5'-bis(azidomethyl)fluoresceine) in FIG. 6 is produced by the following procedure. To a mixture of 4',5'-bis(bromomethyl) fluoresceine dibenzoate (145 mg, 0.2 mmol) and $NaN_3$ (65 mg, 1 mmol) was added 2 ml anhydrous DMSO and the reaction mixture was stirred at room temperature for 16 h. The reaction mixture was treated with NaOH (1 mL of 1M aqueous solution) and after 1 hour acidified with excess of 1M HCl. The resultant precipitate was collected by filtration, dried on air, and purified by flash chromatography (25:1 $CH_2Cl_2/CH_3OH$) to yield title compound (75 mg, 85%) as a yellow-brown solid. $^1$H NMR (400 MHz, DMSO-$d_6$): δ 4.54 (s, 4H), 6.40 (d, J=8.8 Hz, 2H), 6.47 (d, J=8.8 Hz, 2H), 7.01 (d, J=7.6 Hz, 1H), 7.29 (t, J=7.6 Hz, 1H), 7.40-7.46 (m, 1H), 7.51 (t, J=7.2 Hz, 1H), 7.84 (d, J=7.6 Hz, 1H), 7.92 (d, J=7.2 Hz, 1H). $^{13}$C NMR (100 MHz, DMSO-$d_6$): δ 43.42, 109.60, 110.53, 112.73, 124.33, 125.30, 126.71, 128.43, 128.98, 129.78, 129.87, 130.07, 133.40, 135.25, 150.54, 152.29, 158.19, 170.20, 170.29.

According to this example is the sequential derivatization of protein A with an alkynyl group followed by introduction of fluorescent group through 1,3-dipolar addition. Three parallel experiments using: (a) copper(II) acetate; (b) zinc (II) acetate; and (c) blank without addition of any metal cation were all conducted using the same protocol. A solution of ester 27b (10 µL of 0.5 mM solution in methanol) is added to mixture of Protein A (25 µL of 0.1 mM solution in water), metal salt (copper(II) acetate, or zinc acetate, or none in the blank experiment, 10 µL of 0.5 mM solution in water), N-methylimidazole (12 µL of 2.5 mM solution in methanol), methanol (50 µL), and water (50 µL). The reaction mixture was incubated for 48 h at 25° C. followed by addition of imidazole (10 µL of 25 mM solution in methanol) to quench the reaction and prevent possible intramolecular alkylation of Protein A during the subsequent concentration stage. Reaction mixture was evaporated using SpeedVac system followed by addition under argon of diazide 28 (10 µL of 1.5 mM solution in methanol), sodium ascorbate (10 uM of 10 mM solution in water), and CuSO4 (10 μL of 0.5 mM solution in water) and tris[(1-benzyl-1H-1,2,3-triazol-4-yl) methyl]amine (TBTA, 4 μL or 2.5 mM solution in methanol). The reaction mixture was incubated to 48 h at 25° C. in the darkness. Reaction mixtures were separated by SDS-PAGE using 10% separating polyacrylamide gel and 4% stacking gel In-Gel fluorescence imaging was performed using Bio-Rad Gel Doc XR imaging system and Quantity One 1D analysis software.

Fluorescent images were obtained from the same sample at increasing levels of fluorescence threshold. In all images the left stop corresponds to the experiment with $Cu^{2+}$, middle to $Zn^{2+}$, and the right spot to the blank experiment in the absence of metal cations.

Although the present invention has been described in connection with a preferred embodiment, it should be understood that modifications, alterations, and additions can be made to the invention without departing from the scope of the invention as defined by the claims.

What is claimed is:

1. A method for the selective derivatization of a recombinant protein, the method comprising:
   contacting a recombinant protein comprising an oligohistidine tag with a modifying compound in the presence of a metal cation, wherein the modifying compound comprises the formula $X_1X_2X_3$, wherein:
   $X_1$ is an imidazole reactive group comprising the structure represented by the formula:

wherein R1 is an electron withdrawing group and R2 is a connector connecting the imidazole reactive group to $X_2$;
   $X_2$ is a linking group; and
   $X_3$ is at least one ligating group;
   wherein said contacting is performed under conditions sufficient for the formation of a bond between $X_3$ and the oligohistidine tag utilizing said metal cation, and under conditions sufficient for the formation of a covalent bond between $X_1$ and an imidazole ring of the oligohistidine tag and concomitant separation of $X_1$ and $X_2$; and
   breaking the bond between $X_3$ and the oligohistidine tag using a metal chelator.

2. The method of claim 1, wherein said electron withdrawing group is selected from the group consisting of an acyl group, an ester group, an alkylsulfonyl group, an arylsulfonyl group, a nitro group, a cyano group, a carbamoyl group, and combinations thereof.

3. The method of claim 1, wherein $X_3$ comprises a plurality of ligating groups.

4. The method of claim 1, wherein $X_3$ is selected from the group consisting of a primary amino group, a secondary amino group, a teriary amino group, a carboxy group, an imino group, a phenol group, a catechol group, a hydroxamate group, a sulfamido group, a phosphoryl group, an imidazolyl group, a thiazolyl group, an oxazolyl group, a pyridazolyl group, a pyridyl group, a thiol group, and combinations thereof.

5. The method of claim 1, wherein said metal cation is selected from the group consisting of $Ni^{2+}$, $Zn^{2+}$, $Cu^{2+}$, $Fe^{2+}$, $Co^{2+}$, $Co^{3+}$, $Fe^{3+}$, and combinations thereof.

6. The method of claim 1, wherein said conditions sufficient for the formation of a bond between $X_3$ and the oligohistidine tag comprise the presence of an additive.

7. The method of claim 6, wherein the additive comprises imidazole, N-methylimidazole, or N-alkylimidazole.

8. A compound for the selective derivatization of a recombinant protein comprising an oligohistidine tag, the compound comprising:
   the formula $X_1X_2X_3$, wherein $X_1$ is an imidazole reactive group comprising the structure represented by the formula:

wherein R1 is an electron withdrawing group and R2 is a connector connecting the imidazole reactive group to $X_2$;
   $X_2$ is a linking group; and
   $X_3$ is at least one ligating group;
   wherein said compound is adapted to form a bond between $X_3$ and a oligohistidine tag of a recombinant protein in the presence of a metal cation, and further adapted to form a covalent bond between $X_1$ and an imidazole ring of the oligohistidine tag.

9. The compound of claim 8, wherein $X_3$ comprises a plurality of ligating groups.

10. The compound of claim 8, wherein $X_3$ is selected from the group consisting of a primary amino group, a secondary amino group, a teriary amino group, a carboxy group, a phosphoryl group, an imidazolyl group, a thiazolyl group, an oxazolyl group, a pyridazolyl group, a pyridyl group, and combinations thereof.

11. A method for the selective derivatization of a recombinant protein, the method comprising:
   contacting a recombinant protein comprising an oligohistidine tag with a modifying compound in the presence of a metal cation, wherein the modifying compound comprises the formula $X_1X_2X_3$,
   wherein
   $X_1$ is an imidazole reactive group comprising the structure represented by the formula below:

wherein R1 is an electron withdrawing group selected from the group consisting of an acyl group, an ester group, an alkylsulfonyl group, an arylsulfonyl group, a nitro group, a cyano group, and combinations thereof, and R2 is a linker to a linking group;

$X_2$ is said linking group; and $X_3$ is a plurality of ligating groups each selected from the group consisting of a primary amino group, a secondary amino group, a teriary amino group, a carboxy group, a phosphoryl group, an imidazolyl group, a thiazolyl group, an oxazolyl group, a pyridazolyl group, a pyridyl group, and combinations thereof;

and further wherein said contacting is performed under conditions sufficient for the formation of a bond between $X_3$ and the oligohistidine tag utilizing a metal cation, and under conditions sufficient for the formation of a covalent bond between $X_1$ and an imidazole ring of the oligohistidine tag and concomitant separation of $X_1$ and $X_2$; and breaking the bond between $X_3$ and the oligohistidine tag using a metal chelator.

* * * * *

UNITED STATES PATENT AND TRADEMARK OFFICE
CERTIFICATE OF CORRECTION

| | | |
|---|---|---|
| PATENT NO. | : 9,441,010 B2 | Page 1 of 1 |
| APPLICATION NO. | : 13/962426 | |
| DATED | : September 13, 2016 | |
| INVENTOR(S) | : Artem Melman | |

It is certified that error appears in the above-identified patent and that said Letters Patent is hereby corrected as shown below:

In the Specification

Please insert the following after Column 1, Line 13:

--STATEMENT REGARDING FEDERALLY SPONSORED RESEARCH OR DEVELOPMENT
This invention was made with Government support under the National Science Foundation Award 1150768. The United States Government has certain rights in the invention.--

Signed and Sealed this
Thirteenth Day of March, 2018

Andrei Iancu
*Director of the United States Patent and Trademark Office*